(12) United States Patent
Li et al.

(10) Patent No.: US 12,055,555 B2
(45) Date of Patent: Aug. 6, 2024

(54) ON-LINE MEASUREMENT FOR EMITTED AEROSOL PRECURSORS FROM INDUSTRIAL SOURCES

(71) Applicant: FUDAN UNIVERSITY, Shanghai (CN)

(72) Inventors: Qing Li, Shanghai (CN); Anlin Liu, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 323 days.

(21) Appl. No.: 17/501,121

(22) Filed: Oct. 14, 2021

(65) Prior Publication Data

US 2022/0120771 A1    Apr. 21, 2022

(30) Foreign Application Priority Data

Oct. 16, 2020    (CN) .......................... 202011108924.5

(51) Int. Cl.
*G01N 35/00*    (2006.01)
*B01D 5/00*    (2006.01)
(Continued)

(52) U.S. Cl.
CPC ..... *G01N 35/00584* (2013.01); *B01D 5/0012* (2013.01); *B01D 5/0051* (2013.01);
(Continued)

(58) Field of Classification Search
CPC .... B01D 2258/0283; B01D 2258/0233; B01D 2258/0291; B01D 2258/06; B01D 2202/00; F23J 15/00; F23J 2215/20
See application file for complete search history.

(56) References Cited

U.S. PATENT DOCUMENTS 3,969,482 A * 7/1976 Teller .................... B01D 53/60
423/243.08
4,208,383 A * 6/1980 Kisters .................. B01D 53/34
422/111

(Continued)

FOREIGN PATENT DOCUMENTS

| CN | 208547262 U | * | 2/2019 | ................ F28B 1/02 |
| CN | 111298588 B | * | 5/2022 | ............ B01D 17/02 |
| WO | WO-2019029835 A1 | * | 2/2019 | |

*Primary Examiner* — Alexander A Mercado
*Assistant Examiner* — Rodney T Frank
(74) *Attorney, Agent, or Firm* — Ware, Fressola, Maguire & Barber LLP

(57) ABSTRACT

An on-line measurement system for aerosol precursors emitted from industrial sources has three parts: online measurement part, pipeline cleaning part and automatic control part. The system includes: a particulate filter, high temperature intake pipe, two detergent tanks, an air pump, a cooling water pump, two detergent pumps, a condenser, an impinger, a cooling water meter, a salinity meter, a liquid flow meter, a gas flow meter, nitrogen cylinders, connecting pipes, control valves, computer control program etc. The aerosol precursor concentration Cg emitted from industrial sources is measured in the online measurement section. After every measurement, the pipeline is cleaned by the pipeline cleaning part to remove organic and inorganic residual. The automatic control part is controlled by the computer through a controlling program to control the working process of the system. The system has small area occupation, low investment cost, simple maintenance, convenient transformation and high applicability.

10 Claims, 1 Drawing Sheet

(51) Int. Cl.
  *B08B 9/032* (2006.01)
  *G01N 33/00* (2006.01)
  *G01N 35/10* (2006.01)

(52) U.S. Cl.
  CPC ......... *B01D 5/0072* (2013.01); *B01D 5/0096* (2013.01); *B08B 9/0325* (2013.01); *B08B 9/0328* (2013.01); *G01N 33/0036* (2013.01); *G01N 35/10* (2013.01); *B08B 2209/032* (2013.01); *G01N 2035/00445* (2013.01); *G01N 2035/00475* (2013.01)

(56) References Cited

U.S. PATENT DOCUMENTS

| | | | | |
|---|---|---|---|---|
| 4,604,269 A * | 8/1986 | Yoon | .................... | B01D 53/508 423/243.1 |
| 5,085,843 A * | 2/1992 | Rasmussen | .......... | B01D 53/501 423/243.11 |
| 5,435,980 A * | 7/1995 | Felsvang | ................. | B01D 53/64 423/239.1 |
| 6,808,692 B2 * | 10/2004 | Oehr | ...................... | B01D 53/64 423/491 |
| 7,618,602 B2 * | 11/2009 | Meserole | ............. | B01D 53/505 423/243.08 |
| 7,628,969 B2 * | 12/2009 | Holmes | .................. | B01D 53/64 423/243.08 |
| 7,887,769 B1 * | 2/2011 | Smith | ....................... | C01F 5/40 423/243.08 |
| 8,167,975 B2 * | 5/2012 | Shimamura | ........... | B01D 53/64 96/111 |
| 10,557,378 B2 * | 2/2020 | Guethe | .................... | F23J 15/08 |
| 10,633,271 B2 * | 4/2020 | Ji | ............................ | C02F 1/048 |
| 10,775,041 B2 * | 9/2020 | Hughes | ................. | F27D 17/004 |
| 11,325,850 B2 * | 5/2022 | Kamiyama | ............ | B01D 53/32 |
| 2007/0231230 A1 * | 10/2007 | Meserole | ............ | B01D 53/505 423/220 |
| 2016/0214027 A1 * | 7/2016 | Fukuda | ...................... | B01J 2/04 |

* cited by examiner

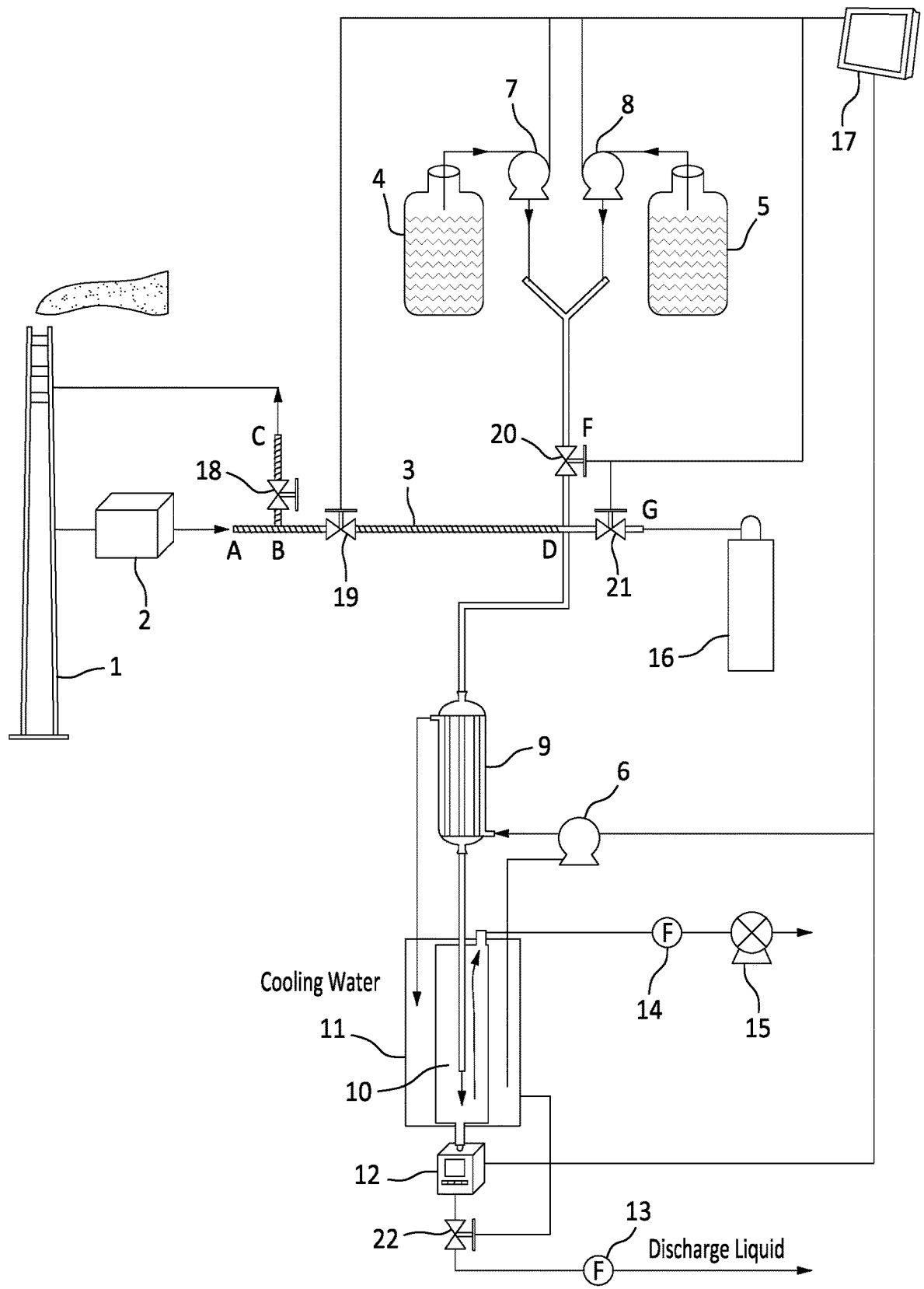

ON-LINE MEASUREMENT FOR EMITTED AEROSOL PRECURSORS FROM INDUSTRIAL SOURCES

CROSS REFERENCE TO RELATED APPLICATIONS

This application claims priority under 35 USC § 119 to Chinese Patent Application No. 202011108924.5 filed on Oct. 16, 2020, which is hereby incorporated by reference in its entirety.

TECHNICAL FIELD

The present invention relates to the field of environmental protection technology, and is specifically an on-line measurement system and method related to the industrial source emission, especially the flue gas aerosol precursor discharged from fixed sources

BACKGROUND ART

Many aerosol precursors are gaseous in chimneys, and PM2.5 (mainly inorganic salts) is formed by condensation after discharging into the ambient air, which makes the actual emission of particulate matter seriously underestimated.

At present, fixed sources mainly use continuous emission monitoring system to detect the emission of solid particulate matter in the flue gas, but it cannot detect the aerosol precursor in the flue gas. Therefore, the invention has great significance for the detection of aerosol precursor concentration emitted from industrial sources, and provides technical support for the detection of particulate matter emission in the post ultra-low emission era.

SUMMARY OF THE INVENTION

In order to more conveniently, efficiently, accurately and real-timely detect the concentration of derived aerosol precursors, so as to accurately detect the concentration of derived particulate matter, and overcome the problems of cumbersome offline detection equipment, complex sampling, complex subsequent analysis and lagging analysis results. The invention provides an on-line detection system and method for aerosol precursors emitted from industrial sources.

The present invention provides an automatic detection system for aerosol precursors emitted from industrial sources, as shown in FIG. 1. The system is divided into three parts: on-line measurement part, pipeline cleaning part and automatic control part, which specifically includes:

- the particulate filter (2) is linked to the chimney (1) to filter solid particles from the flue gas transported in the chimney (1);
- the intake pipe (3) is linked to the filter (2) to make the oversaturated high temperature flue gas maintain gas state before it enters the condenser;
- the impinger (10) is linked to the upper port of the condenser (9) to rapidly reduce the flue gas temperature and the condensed droplets are enriched at the bottom of the impinger (10) through inertial force and flow into the salinity meter;
- the nitrogen cylinder (16) is linked to the upper port of the condenser (9) to purge and dry the pipeline;
- the cooling water meter (11) is linked to the impinger (10) to maintain the water between the range of 0-30° C.;

- the salinity meter (12) is linked to the bottom of the impinger (10) to measure the salinity of condensate;
- the liquid flowmeter (13) is linked to the salinity meter (12) to measure the flow rate of condensate;
- the gas flow meter (14) is linked to the upper part of the impinger (10) to measure the flow rate of flue gas;
- the air pump (15) is linked to the gas flow meter (14) to provide power for the extraction of flue gas;
- W2 detergent tank (4) is used for storing W2 detergent. W2 detergent is a volatile organic solvent for removing residual organic salts in the pipeline;
- W3 detergent tank (5) is used to hold W3 detergent, W3 detergent is deionized water which is used to remove residual inorganic salt in the pipeline;
- the W2 detergent pump (7) is linked to W2 detergent tank (4) to extract W2 detergent into the vertical section of the high-temperature inlet pipe (DF section), the condenser pipe, the impinger and the salinity meter pipe in turn, so as to remove the residual organic salts in the pipe wall;
- the W3 detergent pump (5) is linked to W3 detergent tank (8) to extract W2 detergent into the vertical section of the high-temperature inlet pipe (DF section), the condenser pipe, the impinger and the salinity meter pipe in turn, so as to remove the residual organic salts in the pipe wall;
- the cooling water pump (6) is linked to the condenser (9) to pump the cooling water into the inlet of the lower part of the condenser (9) shell to provide cooling water for the condenser shell.

V1-V5 valves are also set on the system pipeline; V1-V5 valves are solenoid valves;

- the V1 valve (18) is linked to the pipeline BC, the pipeline BC is the pipeline drawn from the intake pipe (3), and B is the connection point between the pipeline BC and the intake pipe (3); the V1 valve (18) is used to control whether the pipeline BC is a pathway, namely to control whether the smoke can return to the chimney.

The V2 valve (19) is set on the BD section of the intake pipe (3), and D is the connection point between the intake pipe (3) and the connecting pipe above the condenser (9). The V2 valve (19) is used to control whether the pipeline BD is a pathway, namely to control whether the high temperature flue gas can enter the condenser (9).

The V3 valve (20) is set on the pipeline DF, and F is the intersection point of the condenser (9) and the inlet pipeline of W2 and W3 detergent tanks. The V3 valve (20) is used to control whether the pipeline DF is a pathway, namely to control whether the detergent can flow into the pipeline DF, condenser (9) and the subsequent pipeline.

The V4 valve (21) is set on the pipeline DG, and G is the connection point between the intake pipe (3) and the outlet of the nitrogen cylinder (16). The V4 valve (21) is used to control whether the pipeline DG is a pathway, namely to control whether the nitrogen can be used to purge and dry the condensing pipeline.

The V5 valve (22) is set between the salinity meter (12) and the liquid flow meter (13), close to the outlet of the salinity meter (12), to control whether the drainage pipeline is a pathway, namely to control whether condensate and detergent can flow out of the pipeline.

It also includes a computer which controls the working process of the testing system through the control procedure and the control panel.

Based on the devices above, the automatic detection method of aerosol precursors emitted from industrial sources is as follows:

(1) on-line measurement: under the action of the air pump (15), the oversaturated high temperature flue gas in chimney (1) is filtered through the particulate filter (2), the particulate matter in the flue gas is removed, and then enters the intake pipe (3), and the wall temperature of the intake pipe (3) is controlled to be 120-130° C., so that the flue gas remains gaseous and does not attach residues to the pipeline. The oversaturated high temperature flue gas enters the condenser (9), the temperature of the flue gas decreases rapidly after condensation, and the gas condenses into droplets in the condenser and then enters the impinger (10). In the process of entering the impinger (10), the temperature of the flue gas further decreases, and the droplet size further increases. Through inertia force, the droplets are collected and enriched in the bottom of the impinger, and flow into the salinity meter (12) to measure the salinity value. Then the liquid flow rate is measured through the liquid flow meter (13), and discharges the liquid at last. Simultaneously, a very small amount of liquid entrained by gas flows out of the exhaust port above the impinger (10) and pass through the gas flow meter (11) to obtain the gas flow value, and then the gas is discharged by the air pump (15);

The calculation formula of aerosol precursor concentration Cg emitted from industrial sources is: $Cg=K*(Vw*Cw)/Vg$. Among them, Vw is condensate volume, Cw is condensate salinity, Vg is gas extraction volume, K is empirical constant;

(2) Pipeline cleaning: when the salinity meter (12) completes one salinity measurement of the condensate, the W2 detergent pump (7) extracts the W2 detergent in the W2 detergent tank (4) into the pipeline to clean the pipeline. After a period of cleaning, W2 detergent pump (7) stops working. Then the W3 detergent pump (8) extracts the W3 detergent into the pipeline to clean the pipeline. After a period of cleaning, the W3 detergent pump (8) stops working; W2 and W3 detergent is discharged from the bottom of the impinger (10), passing through salinity meter (12) and liquid flow meter (13). Then the V4 valve (21) is opened, the nitrogen in the nitrogen cylinder (16) enters the pipeline to purge and dry the wet pipeline, and the V4 valve (21) is closed after a period of time.

The computer controls the work of the cooling water pump (6), the W2 detergent pump (7), the W3 detergent pump (8), the air pump (15) and the V1-V5 valves through a controlling program. The specific control process is:

When the heating pipe temperature rises and maintains at 120-130° C., open the V2 valve (19), close the V1 valve (18). Then, the air pump (15) and the cooling water pump (6) are opened, and the cooling water in the cooling water meter (11) is pumped into the condenser (9) shell. When the condensate water is enriched in the salinity meter (12) and reaches a certain height, the salinity meter (12) can accurately measure the salinity of the condensate. The air pump (15) stops working, the V2 valve (19) and the V1 valve (18) are closed, and the V5 valve (22) is opened, so that the condensate of the salinity meter (12) is discharged after passing through the liquid flow meter (13). Then the V3 valve (20) and the W2 detergent pump (7) are opened; the W2 detergent is extracted from the W2 detergent tank (4) to clean the pipeline, and the liquid is discharged after passing through the impinger (10), the salinity meter (12) and the liquid flow meter (13). Then the W3 detergent pump (8) is opened, the W3 detergent is extracted from the W3 detergent tank (5) to clean the pipeline, and the liquid is also discharged after passing through the impinger (10), the salinity meter (12) and the liquid flow meter (13). Then the V3 valve (20) is closed, the V4 valve (21) is opened, and the nitrogen in the nitrogen cylinder (16) purges the pipeline. After the purging, the V4 valve (21), V5 valve (22), V1 valve (18) are closed, and the V2 valve (19) is opened to prepare for the next round of on-line measurement of aerosol precursors.

In the invention, the filtration efficiency of the particulate filter (2) is above 99%, and the filter can replace and clean the filter membrane itself when the pump is not working.

In the invention, the temperature of the intake pipe (3) is always maintained at 120-130° C. (preferably 125° C.), which effectively prevents the condensation and adhesion of the flue gas in the pipeline.

In the invention, the cooling water is pumped into the inlet of the lower shell of the condenser through the cooling water pump (6), and then flows out from the outlet of the upper shell of the condenser to enter the cooling water meter (11), the temperature of the oversaturated high temperature flue gas in the condenser decreases rapidly, and the droplets precipitate after condensation.

In the invention, the impinger (10) is linked in series with the gas outlet of the condenser (9), the grown droplets are enriched at the bottom of the impinger through inertial force and flow into the salinity meter (12). There is also a gas outlet at the upper part of the impinger, which is linked to the gas flow meter (14) and the air pump (15).

In the invention, the cooling water temperature in the cooling water meter (11) is adjustable within 0-30° C.

In the invention, the gas flow meter (14) and the liquid flow meter (13) can accurately measure the medium flow and liquid flow, and the specific values are fed back to the automatic control panel.

In the invention, when cleaning the pipeline, the opening time of the W2 detergent pump and the W3 detergent pump is 8-12 min, which can be adjusted according to different emission sources.

In the invention, when the pipeline is purged, the flow rate of nitrogen is controlled to be 8-12 L/min, which can be adjusted according to different emission sources.

In the invention, W2 detergent is preferably methanol solution.

The control system of the invention can adjust the extraction flow rate and time by controlling the cooling water pump (6), the W2 detergent pump (7) and the W3 detergent pump (8).

The control system of the invention, including manual and automatic control systems, which can be switched to manual or automatic operation at any time.

The features of the invented method are as follows:

(1) Compared with the traditional weighing method and titration method, this method can quickly detect the salinity of flue gas, and can complete the detection of aerosol precursors discharged from industrial sources in an average of 1 hour.

(2) The aerosol precursor concentration emitted from industrial sources can be detected automatically, and the online detection of aerosol precursor concentration emitted from industrial sources can be realized.

(3) The device can be directly linked to the existing flue gas measuring devices and has strong modification.

The features of the invention are as follows:

(1) The device has a small floor area, simple installation and low maintenance cost.

(2) After each measurement, the device can automatically clean and purge the pipeline to prevent interference to the next measurement.

(3) The device can record the measurement data real-timely, and the data is synchronized to the host computer to achieve remote monitoring.

DESCRIPTION OF FIGURES

FIG. 1 is the illustration of the on-line measurement system for aerosol precursors emitted from industrial sources.

The labels in the figure are as follows: 1 chimney, 2 particulate filter, 3 intake pipe, 4 W2 detergent tank, 5 W3 detergent tank, 6 cooling water pump, 7 W2 detergent pump, 8 W3 detergent pump, and 9 condenser, 10 for impinger, 11 cooling water meter, 12 salinity meter, 13 liquid flow meter, 14 gas flow meter, 15 air pump, 16 nitrogen cylinder, 17 computer, 18 V1 valve, 19 V2 valve, 20 V3 valve, 21 V4 valve, 22 V5 valve.

DETAILED DESCRIPTION OF THE INVENTION

The invention is further described in combination with the field test of the invention in a coal-fired power plant, but the protection scope of the invention is not just limited to this.

As shown in FIG. 1, an automatic detection system for aerosol precursors emitted from industrial sources, including 1 chimney, 2 particulate filter, 3 intake pipe, 4 W2 detergent tank, 5 W3 detergent tank, 6 cooling water pump, 7 W2 detergent pump, 8 W3 detergent pump, and 9 condenser, 10 for impinger, 11 cooling water meter, 12 salinity meter, 13 liquid flow meter, 14 gas flow meter, 15 air pump, 16 nitrogen cylinder, 17 computer, 18 V1 valve, 19 V2 valve, 20 V3 valve, 21 V4 valve, 22 V5 valve.

The technical thought of the invention is as follows:

Under the action of the air pump, after the oversaturated high-temperature flue gas in the chimney passes through the particulate filter, the particulate matter in the flue gas is removed, and then enters the intake pipe with the pipe wall temperature of 125° C., which keeps the flue gas in gaseous state to avoid adhesion and residual in the pipeline. After the oversaturated high temperature flue gas enters the condenser, the temperature decreases rapidly, and the aerosol precursors dissolve rapidly in the droplet and form saltness. Condenser is a shell-and-tube heat exchanger, the oversaturated high-temperature flue gas passes through the condenser tube, and the cooling liquid passes through the condenser shell. Under the action of cooling water pump 6, the cooling water in the cooling water meter is pumped into the lower shell inlet of the condenser, and flows out from the upper shell outlet and enters the cooling water meter. The gas condenses into droplets in the condenser and enters the impinger. In the process of entering the impinger, the flue gas temperature further decreases, and the droplet size further increases. Under the action of inertial force, the droplets gather at the bottom of the impinger and flow into the salinity meter, and the condensate is discharged through the liquid flow meter after measuring the salinity. Simultaneously, a very small amount of liquid entrained by gas is discharged from the outlet above the impinger through the flow meter and the air pump.

When the salinity meter completes one measurement of the salinity of the condensate, under the action of the W2 detergent pump, W2 detergent is pumped into the pipeline to clean the pipeline. After a period of cleaning, the W2 detergent pump stops working. Then the W3 detergent pump extracts the W3 detergent into the pipeline and cleans the pipeline. After a period of cleaning, the W2 detergent pump stops working. W2 and W3 detergent is discharged from the bottom of the impinger through salinity meter and liquid flow meter. Then the V4 valve is opened, and nitrogen enters the pipeline to clean and dry it. After a period of purging, the V4 valve is closed to prepare for the next round of measurement.

In the invention, the intake pipe temperature can be maintained at about 125° C.

In the invention, the temperature of cooling water in the cooling water meter is adjustable within 0-30° C.

In the invention, the flow rate of the air pump is adjustable within 0-30 L/min.

In the invention, W2 detergent mainly removes the organic salts that may be left in the pipeline, and W3 detergent mainly removes the inorganic salts that may be left in the pipeline to prevent interference in the next round of measurement. The cleaning time and the power of the liquid pump can be adjusted.

In the invention, the separation efficiency of the impinger for condensed droplets in gas is above 90%.

In the invention, only 50 ml condensate is needed, and the salinity of condensate is accurately measured by salinity meter.

All the documents mentioned in this invention are cited as references in this application, just as each document is cited as an independent reference. In addition, after reading the contents of the invention above, technicians in this field can change or modify the invention variously, and these equivalent forms are also suitable for the scope of the claims attached to the application.

What is claimed is:

1. A system for detecting aerosol precursors in a flue gas emitted from an emitting source, said system comprising:
    a particulate filter;
    a temperature-maintaining pipe;
    a gas condenser;
    an impinger; and
    a salinity meter, wherein
    the particulate filter is configured to remove particulates in the flue gas and to provide a filtered flue gas,
    the gas condenser is configured to receive the filtered flue gas from the particulate filter through the temperature-maintaining pipe and to provide condensed liquid droplets from the filtered flue gas, the condensed liquid droplets containing dissolved therein the aerosol precursors as salt;
    the impinger is operatively connected to the gas condenser for collecting the condensed liquid droplets; and
    the salinity meter is configured to measure salinity in the condensed liquid droplets discharged from the impinger, and wherein the temperature maintaining pipe is configured to maintain a temperature of 120-130° C.

2. The system according to claim 1, further comprising a cooling tank configured to provide a cooling liquid to the gas condenser for reducing a temperature of the filtered flue gas received into the gas condenser, wherein the cooling tank is configured to keep a temperature of the cooling liquid between 0-30° C.

3. The system according to claim 2, wherein the impinger is placed inside the cooling tank to be cooled by the cooling liquid.

4. The system according to claim 1, further comprising a liquid flow meter configured to measure a liquid flow rate of the condensed liquid droplets discharged from the impinger.

5. The system according to claim 4, further comprising a gas flow meter configured to measure a gas flow rate of the filtered flue gas.

6. The system according to claim 1, further comprising a nitrogen tank arranged to clean a gas conduit in the temperature-maintaining pipe and the gas condenser.

7. The system according to claim 1, further comprising a deionized water tank arranged to clean the temperature-maintaining pipe and the gas condenser.

8. The system according to claim 1, further comprising an organic solvent tank arranged to clean the temperature-maintaining pipe and the gas condenser.

9. The system according to claim 5, further comprising a computer configured to measure a concentration of the aerosol precursors based on the gas flow rate, the liquid flow rate and the salinity of the condensed liquid droplets.

10. The system according to claim 9, wherein the computer is further configured
- to allow the filtered flue gas from the particulate filter to be received by the gas condenser through the temperature-maintaining pipe when the salinity in the condensed liquid droplets, the liquid flow rate and the gas flow rate are measured, and
- to block the filter flue gas from reaching the temperature-maintaining pipe when the temperature-maintaining pipe, the gas condenser and the impinger are scheduled for cleaning.

* * * * *